US007112194B2

(12) United States Patent
Fujieda

(10) Patent No.: US 7,112,194 B2
(45) Date of Patent: Sep. 26, 2006

(54) METHOD AND APPARATUS FOR OBTAINING IRRADIATION INTENSITY OF A LASER BEAM, AND APPARATUS FOR IRRADIATING THE LASER BEAM

(75) Inventor: Masanao Fujieda, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 286 days.

(21) Appl. No.: 10/626,527

(22) Filed: Jul. 25, 2003

(65) Prior Publication Data

US 2004/0147910 A1 Jul. 29, 2004

(30) Foreign Application Priority Data

Aug. 1, 2002 (JP) ............................. 2002-224334

(51) Int. Cl.
*A61B 18/18* (2006.01)
*A61B 18/20* (2006.01)

(52) U.S. Cl. ............................. 606/10; 606/5; 606/12; 351/212

(58) Field of Classification Search ................ 606/4–6, 606/10–12; 351/208–212
See application file for complete search history.

(56) References Cited

U.S. PATENT DOCUMENTS 4,880,986 A * 11/1989 Yamada et al. .......... 250/484.5
5,507,799 A 4/1996 Sumiya
5,520,679 A 5/1996 Lin
5,624,436 A 4/1997 Nakamura et al.
5,637,109 A 6/1997 Sumiya
5,827,264 A 10/1998 Hohla
5,906,608 A 5/1999 Sumiya et al.
6,203,539 B1 3/2001 Shimmick et al.
6,210,401 B1 4/2001 Lai
6,572,606 B1 * 6/2003 Kliewer et al. ................ 606/5
6,592,574 B1 * 7/2003 Shimmick et al. ............. 606/4
2002/0120198 A1 8/2002 Nakamura

FOREIGN PATENT DOCUMENTS

EP 1 040 797 A2 10/2000

* cited by examiner

*Primary Examiner*—A. Farah
(74) *Attorney, Agent, or Firm*—Rader, Fishman & Grauer PLLC; Ronald P. Kananen

(57) ABSTRACT

A method and an apparatus for obtaining irradiation intensity of a laser beam, and a laser beam irradiation apparatus that enable obtaining an irradiation intensity distribution of a laser beam easily, and attaining more accurate ablation. The method for obtaining an irradiation intensity of a laser beam has the steps of inputting an intensity of fluorescence emitted from a fluorescent glass, the fluorescence intensity being obtained when the laser beam is irradiated onto the fluorescent glass which emits the fluorescence by irradiation of the laser beam with an ablation area of a size required for processing an object to be processed, and obtaining an irradiation intensity distribution of the laser beam in the ablation area based on the inputted fluorescence intensity.

3 Claims, 7 Drawing Sheets

209b
209c
209
209a
208
206
Control Unit
216
217
218
219
220
221
233
203
215
260
222
230
232
231
227
265
268
226
224
225
214
213
212
223
L
Laser Light Source
211
210
250
Ec

METHOD AND APPARATUS FOR OBTAINING IRRADIATION INTENSITY OF A LASER BEAM, AND APPARATUS FOR IRRADIATING THE LASER BEAM

BACKGROUND OF THE INVENTION

1. Field of the Invention

The present invention relates to a method and an apparatus for obtaining irradiation intensity of a laser beam, and an apparatus for irradiating the laser beam.

2. Description of Related Art

Conventionally, an apparatus which irradiates a laser beam is used in a variety of fields for medical treatment and processing. For example, in the field of ophthalmology, there is known a laser irradiation apparatus which changes a corneal curvature by ablating a cornea with irradiation of an excimer laser beam, and to correct a refractive error of an eye. In this kind of apparatus, irradiation intensity distribution in an irradiation area of the laser beam (a cross-sectional area of the laser beam to be irradiated) and/or in an ablation area varies because of time-course change of an irradiation optical system or the like, and consequently, an ablation shape such as ablation depth distribution sometimes varies. Therefore, it is necessary to adjust the laser irradiation according to those variations.

In order to adjust the laser irradiation, the applicant has proposed, in Japanese Patent Application Unexamined Publication No. Hei6-226471 corresponding to U.S. Pat. No. 5,624,436, a method for forming a curved surface on a transparent plate (PMMA plate) having a known ablation rate by laser irradiation so as to have predetermined refractive power, then measuring the refractive power of the curved surface with a lens meter, and calibrating data for ablation based on the measurement result.

According to the above method, it has become possible to easily adjust the laser irradiation in correspondence with the variations in the irradiation intensity distribution and the ablation shape; however, a further technique for attaining more accurate ablation is desired.

SUMMARY OF THE INVENTION

An object of the invention is to overcome the problems described above and to provide a method and an apparatus for obtaining irradiation intensity of a laser beam, and an apparatus for irradiating the laser beam that enable obtaining irradiation intensity distribution of a laser beam easily, and attaining more accurate ablation.

To achieve the objects and in accordance with the purpose of the present invention, a method for obtaining an irradiation intensity of a laser beam has the steps of inputting an intensity of fluorescence emitted from a fluorescent glass, the fluorescence intensity being obtained when the laser beam is irradiated onto the fluorescent glass which emits the fluorescence by irradiation of the laser beam with an ablation area of a size required for processing an object to be processed, and obtaining an irradiation intensity distribution of the laser beam in the ablation area based on the inputted fluorescence intensity.

In another aspect of the present invention, an apparatus for obtaining an irradiation intensity of a laser beam has input means for inputting an intensity of fluorescence emitted from a fluorescent glass, the fluorescence intensity being obtained when the laser beam is irradiated onto the fluorescent glass which emits the fluorescence by irradiation of the laser beam with an ablation area of a size required for processing an object to be processed, and obtaining means for obtaining an irradiation intensity distribution of the laser beam in the ablation area based on the inputted fluorescence intensity.

Yet, in another aspect of the present invention, an apparatus for irradiating the laser beam has irradiation means having a laser source and an irradiation optical system for irradiating a laser beam onto an object to be processed, input means for inputting ablation data for ablating the object to be processed into a predetermined shape by irradiation of the laser beam, control means for obtaining control data for the irradiation means based on the inputted ablation data, a fluorescence detecting optical system having an area sensor, for obtaining an intensity of fluorescence emitted from a fluorescent glass, the fluorescence intensity being obtained when the laser beam is irradiated onto the fluorescent glass which emits the fluorescence by irradiation of the laser beam with an ablation area of a size required for processing the object to be processed, obtaining means for obtaining an irradiation intensity distribution of the laser beam in the ablation area based on the obtained fluorescence intensity, and calibrating means for calibrating at least one of the ablation data or the control data for the irradiation means based on the obtained irradiation intensity distribution.

Additional objects and advantages of the invention are set forth in the description which follows, are obvious from the description, or may be learned by practicing the invention. The objects and advantages of the invention may be realized and attained by the method and apparatus for obtaining irradiation intensity of a laser beam, and the laser beam irradiation apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
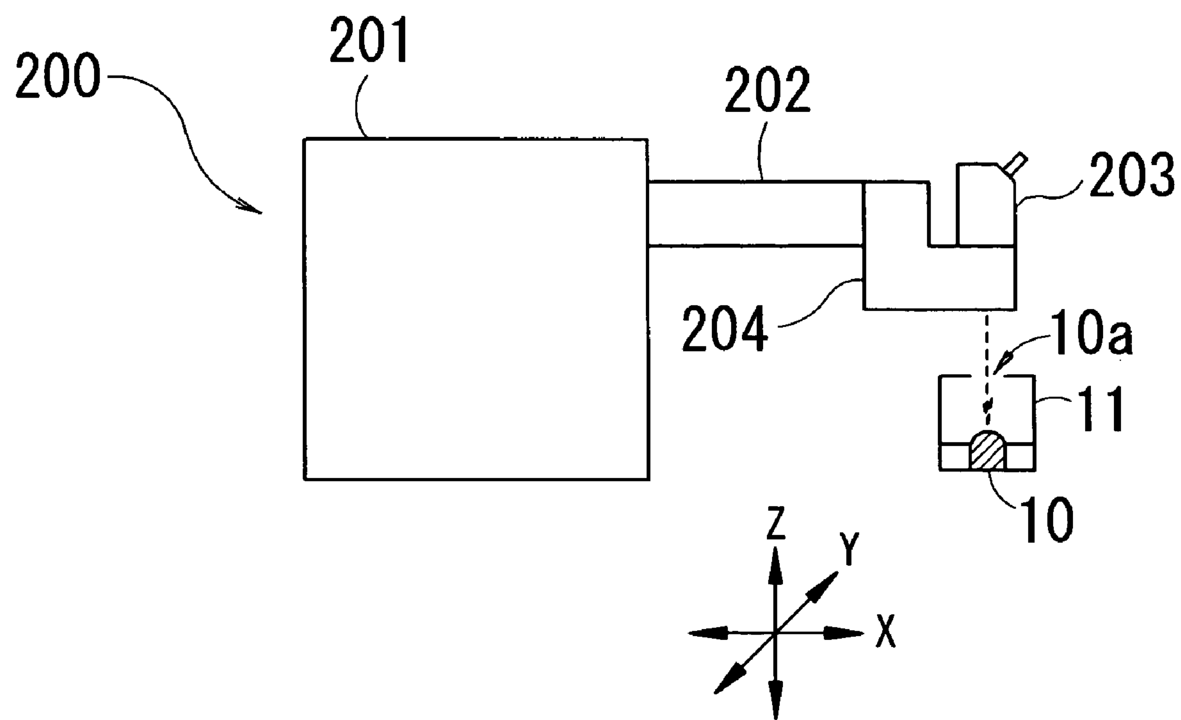
FIG. 1 is a view showing a schematic configuration of an ophthalmic laser irradiation apparatus system consistent with the present invention.

A detailed description of one preferred embodiment of a method and an apparatus for obtaining irradiation intensity of a laser beam, and an apparatus for irradiating the laser beam embodied by the present invention is provided below with reference to the accompanying drawings. FIG. 1 is a view showing a schematic configuration of an ophthalmic laser irradiation apparatus system consistent with the present invention.

A laser beam irradiation apparatus 200 ablates a cornea of a patient's eye with an excimer laser beam. A laser light source and the like are integrated in a main body 201 of the irradiation apparatus 200. A laser beam from the laser light source is guided to an arm unit 202 and an end unit 204 attached to the end of the arm unit 202, and is irradiated onto the cornea of the patient's eye. Arranged inside of the main body 201 to the end unit 204 is an irradiation optical system to be described later. The end unit 204 is provided with a binocular microscope unit 203 for observing the patient's eye. The arm unit 202 is movable in horizontal directions (X and Y directions), and the end unit 204 is movable in a vertical direction (Z direction).

Reference numeral 10 is a fluorescent glass used for measuring irradiation intensity distribution of the laser beam. The fluorescent glass 10 is comprised of a glass component such as $SiO_2$ or $B_2O_3$ and a rare-earth element such as $Tb_2O_3$ or $Eu_2O_3$, and emits visible fluorescence when it is irradiated with ultraviolet rays. A surface to be irradiated of the fluorescent glass 10 may be in a plate shape; however, it is preferably in a shape of a convex-curved surface having a curvature being approximate to that of a corneal shape of a human eye. For example, it is made to have a dome-shaped surface where a radius of curvature R=7.8 mm which is an average radius of curvature of the human eye. A diameter of the dome-shaped surface is 12 mm, and it is preferably 10 mm or more. If the surface to be irradiated of the fluorescent glass 10 is formed into the shape of the convex-curved surface to resemble the cornea, the irradiation intensity distribution may be obtained while power loss due to influences of defocus of the laser beam and inclination of the surface to be irradiated at the time of actual corneal surgery is considered.

Reference numeral 11 is a holder for holding the fluorescent glass 10, and may be in any shape as long as it can stably hold the fluorescent glass 10. A housing of the holder 11 is preferably a shielded cylinder for reducing incidence of disturbance light. The fluorescent glass 10 is provided inside the shielded cylinder of the holder 11. Placed at the top of the shielded cylinder is an opening 10*a* for having the laser beam enter and passing the emitted fluorescence.

Figure 2:
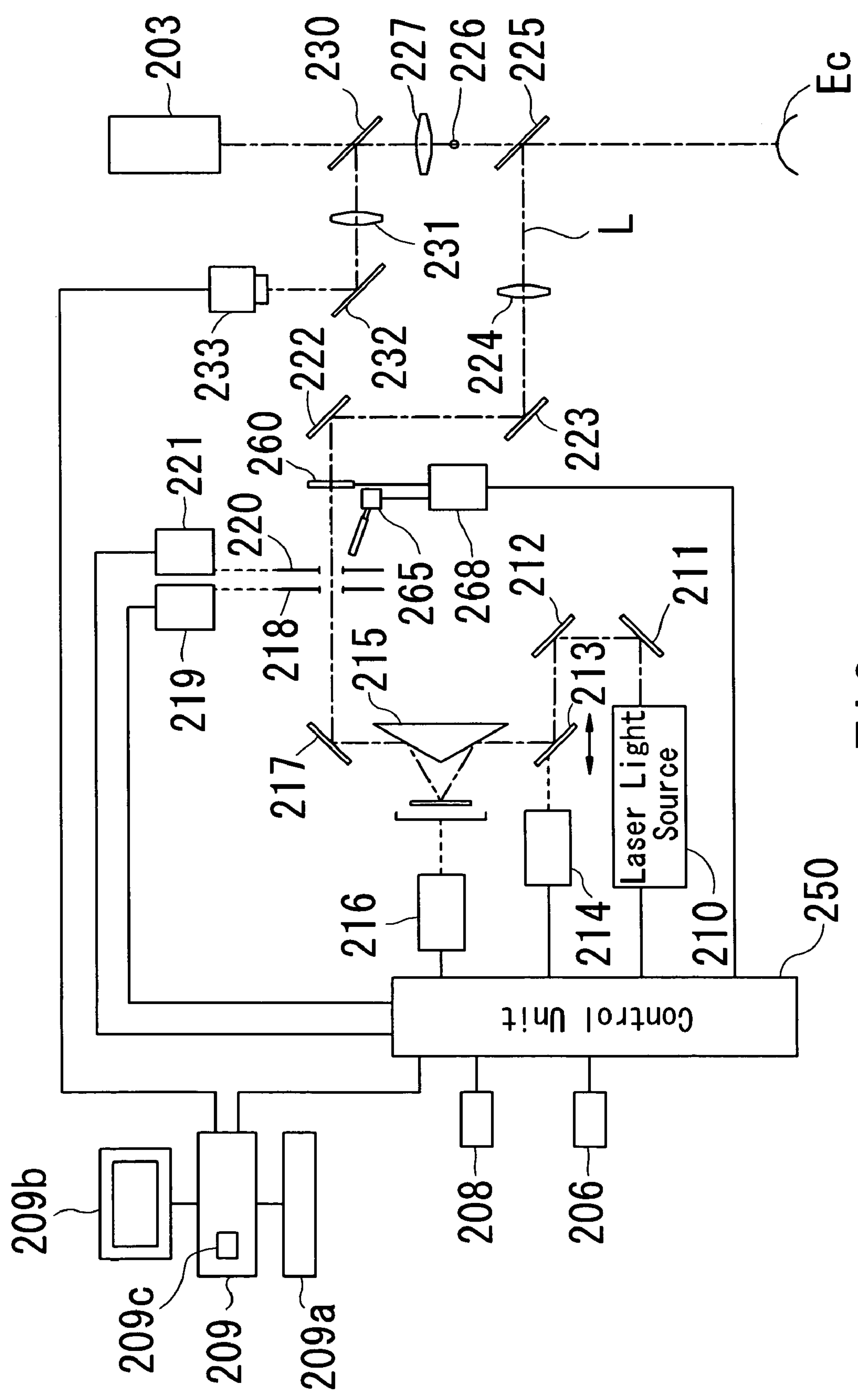
FIG. 2 is a view showing a schematic configuration of an irradiation optical system and a control system in a laser irradiation apparatus.
Figure 3:
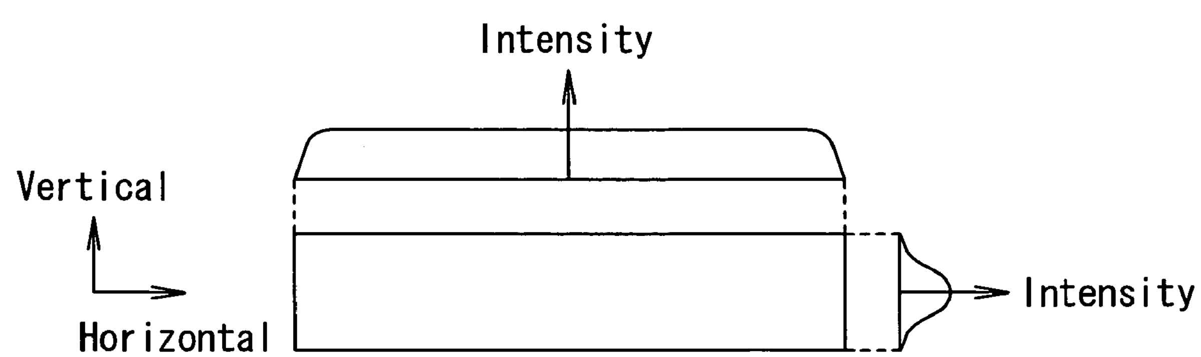
FIG. 3 is a view illustrating a typical shape of an excimer laser beam.

FIG. 2 is a view showing a schematic configuration of the irradiation optical system and a control system in the irradiation apparatus 200. The laser light source 210 emits an excimer laser beam with a wavelength of 193 nm. From the laser source 210, a laser beam of which a cross section is in a rectangular shape is generated and emitted as shown in FIG. 3. Intensity distribution in a horizontal direction of the emitted laser beam is approximately uniform, and intensity distribution in a vertical direction is the Gaussian distribution. The laser beam emitted from the laser source 210 is reflected by mirrors 211 and 212, and further reflected by a plane mirror 213. The mirror 213 is translatable (movable) in a direction of the arrow shown in FIG. 2 by a mirror driving unit 214, and translates (scans) the laser beam in the Gaussian distribution direction.

An image rotator 215 is rotatably driven about a central optical axis L by an image rotator driving unit 216, and rotates the laser beam about the optical axis L. Reference numeral 217 is a mirror.

Reference numeral 218 is a circular aperture having a circular opening for limiting an ablation area to a circular shape, and an aperture driving unit 219 changes an opening diameter thereof. Reference numeral 220 is a slit aperture having a slit opening for limiting the ablation area to a slit shape, and an aperture driving unit 221 changes opening width and direction. Mirrors 222 and 223 change a direction of the beam. A projecting lens 224 projects the openings of the circular aperture 218 and the slit aperture 220 onto the cornea Ec.

Figure 4:
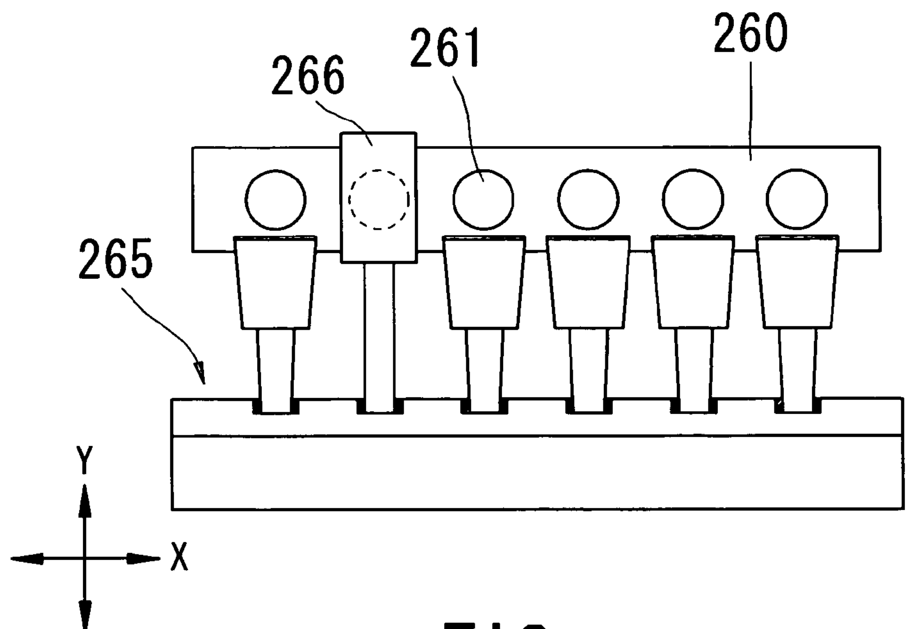
FIG. 4 is a view showing a schematic configuration of a dividing aperture plate and a dividing shutter.

In addition, a dividing aperture plate 260 is disposed insertably and removably on an optical path between the slit aperture 220 and the mirror 222. The dividing aperture plate 260 further limits the ablation area (an irradiation area) in combination with a dividing shutter 265. The dividing aperture plate 260 and the dividing shutter 265 are used when an asymmetric component of the cornea Ec is ablated. When the dividing aperture plate 260 is viewed from the light source 210 side, six small circular apertures 261 of the same size are aligned as shown in FIG. 4. One or more shutter plates 266 of the dividing shutter 265 cover and uncover the small apertures 261 selectively, thereby enabling the ablation area (irradiation area) to be further limited to a small area for the laser irradiation. The dividing aperture plate 260 and the dividing shutter 265 are movable by a driving unit 268 within a plane vertical to the optical axis L.

A dichroic mirror 225 has a property of reflecting an excimer laser beam and transmitting visible light. The laser beam passed through the projecting lens 224 is reflected by the dichroic mirror 225 and directed to and irradiated onto the cornea Ec. Placed above the dichroic mirror 225 are a fixation light 226, an objective lens 227, and the microscope unit 203.

A mirror 230 is disposed between binocular optical paths of the microscope unit 203 (on an optical axis of the objective lens 227). An image forming lens 231, a mirror 232, and a CCD camera 233 as an area sensor are disposed on an optical path at a reflecting side of the mirror 230. The camera 233 is connected to a computer 209. The objective lens 227, the mirror 230, the mirror 232, and the camera 233 constitute an optical system for detecting a luminance (intensity) of the fluorescence emitted from the fluorescent glass 10. The optical system may double as an image-pickup optical system for observing an anterior-segment of the patient's eye. The computer 209 is connected with an input unit 209*a* for inputting surgical data such as data on a pre-operative corneal shape and/or data on a correction amount, and with a monitor 209*b*. The computer 209 is provided with a memory 209*c* for storing image data from the camera 233, and performs processings such as calculation and calibration of data for ablation.

A control unit 250 controls the laser light source 210, each of the driving units and the like. The control unit 250 is connected with a foot switch 208, a controller 206 on which a variety of operation switches are disposed, and the computer 209.

Ablation performed by the laser irradiation apparatus 200 will be described hereinafter. In the case of the ablation with constant depth distribution, the mirror 213 is translated (moved) in the direction of the arrow shown in FIG. 2, and the laser beam in a rectangular shape is translated (scanned) in the Gaussian distribution direction at a rate based on a repetition frequency of a laser pulse from the laser source 210. The mirror 213 is moved in synchronization with the laser pulse. That is to say, after irradiating one pulse (or several pulses) at a certain travel position, the mirror 213 is moved to the next position, and after irradiating one pulse (or several pulses), the mirror 213 is moved again. These operations are repeatedly provided from one end to the other end of the ablation area limited by the opening of the circular aperture 218. Then, every time the laser beam has been moved (scanned) in one direction, the movement (scanning) direction of the laser beam is changed by the rotation of the image rotator 215 at each predetermined angle to perform ablation within the opening of the circular aperture 218. Incidentally, as Japanese Patent Application Unexamined Publication No. Hei4-242644 corresponding to U.S. Pat. No. 5,507,799 and Japanese Patent Application Unexamined Publication No. Hei6-114083 corresponding to U.S. Pat. No. 5,637,109 describe a method for uniformly ablating an object in detail, please refer to it for detail.

In myopic correction, when the ablation is performed deeply at a central part compared with a peripheral part so as to remove a spherical component which is rotationally symmetrical, the following procedure is performed. The laser beam is moved (scanned) in the Gaussian distribution direction within the opening of the circular aperture 218 by moving the mirror 213. Then, every time the laser beam has been moved (scanned) in one direction, the movement (scanning) direction of the laser beam is changed by the rotation of the image rotator 215 to perform ablation within the opening of the circular aperture 218. These processes are performed every time the opening diameter of the circular aperture 218 is sequentially changed. According to these processes, ablation may be performed on the spherical component which is deep at the central part of the cornea Ec and shallow at the peripheral part. In the case of removing a cylindrical component which is linearly symmetrical, the same control is provided using the slit aperture 220 instead of the circular aperture 218.

Further, in the case of partial ablation so as to remove an asymmetric component, the dividing aperture plate 260 is used. The dividing aperture plate 260 is disposed on the optical path of the laser beam to control positions of the small apertures 261 of the dividing aperture plate 260, and selectively open and close the small apertures 261 by driving the dividing shutter 265. By the movement (scanning) of the laser beam caused by the movement of the mirror 213, the laser beam of a small area passing through the opening small apertures 261 is partially irradiated onto the cornea Ec.

In the irradiation apparatus system as provided above, a method for obtaining the irradiation intensity distribution of the laser beam and adjusting the laser irradiation will be described hereinafter. Firstly, the fluorescent glass 10 is disposed at a predetermined position with respect to the irradiation optical system (the optical axis L) in the irradiation apparatus 200. The switches on the controller 206 are operated to put an operation mode of the apparatus into a calibration mode for the irradiation intensity distribution, and the foot switch 208 is pressed for the laser irradiation. In the calibration mode, the opening diameter of the circular aperture 218 is expanded so as to make the size of the ablation area maximized as required for a corneal surgery, and each of the driving units in the irradiation optical system is controlled in the same manner as in the case of the ablation of the object with the constant depth distribution.

By the laser irradiation, the fluorescent glass 10 emits the fluorescence having the luminance corresponding to the irradiation intensity of the laser beam. The fluorescence emitted from the fluorescent glass 10 is photo-received by an image-pickup element of the camera 233. An output signal from the camera 233 is inputted to the computer 209, and a photo-received digital image having light intensity is stored in the memory 209*c*.

Figure 5:
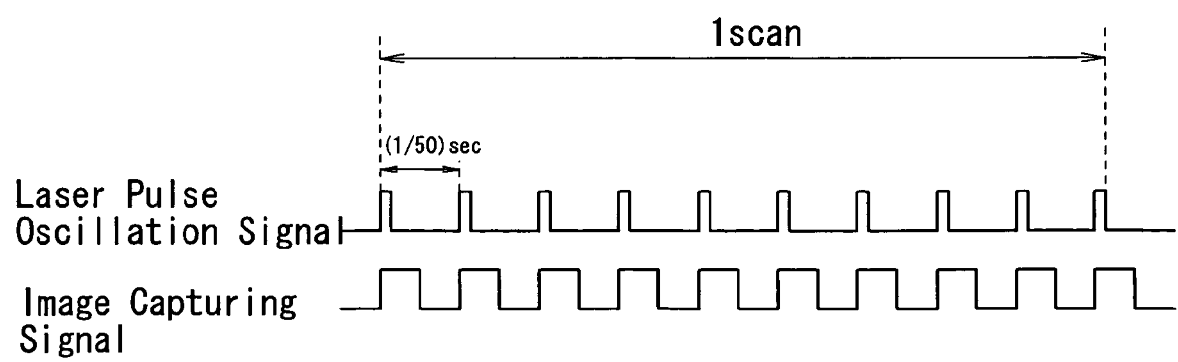
FIG. 5 is a view illustrating synchronization between initiation of image-capturing and oscillation of a laser pulse.
Figure 6A:
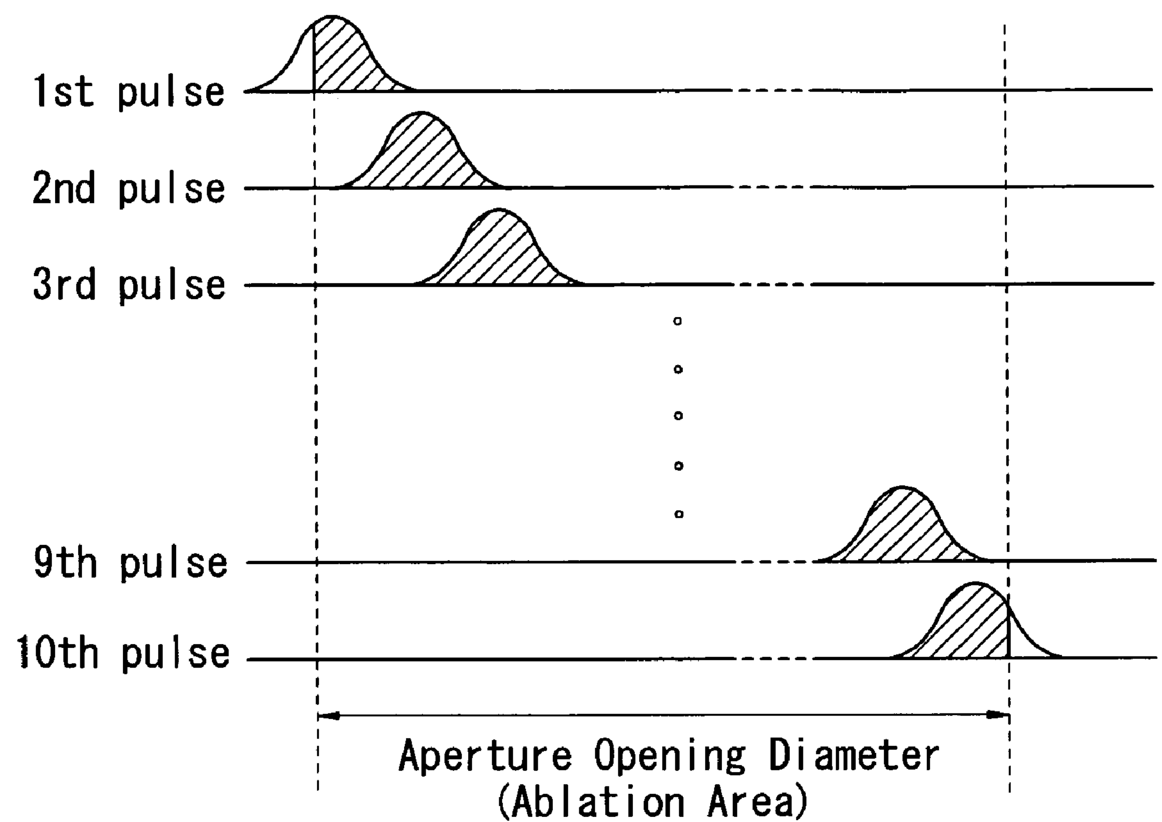
FIGS. 6A and 6B are views illustrating a summation of images captured by a camera.
Figure 6B:
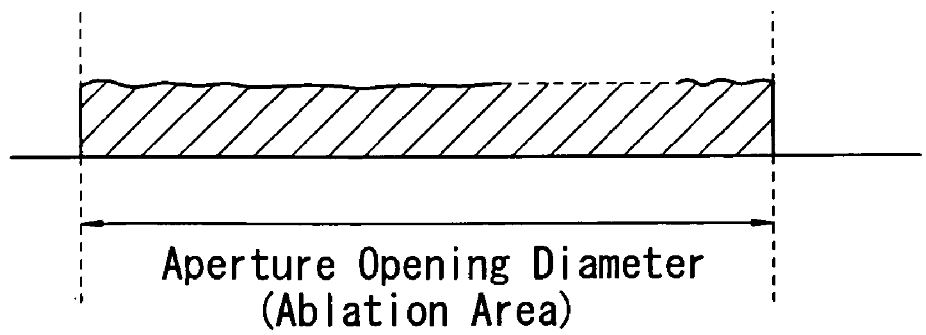

As previously mentioned, at the time of the ablation, the laser beam is moved (scanned) in the Gaussian distribution direction by the movement of the mirror 213. The laser beam is moved (scanned) in synchronization with the laser pulse, and the uniform ablation is attained by scanning the pulsed laser beam (see Japanese Patent Application Unexamined Publication No. Hei5-220189 corresponding to U.S. Pat. No. 5,637,109). For example, the laser irradiation in one direction (one scan) in the ablation area limited by the opening of the circular aperture 216 is assumed to be attained with ten pulses. In the case of capturing a fluorescent image, an image capturing signal of the camera 233 is synchronized to a laser pulse oscillation signal as shown in FIG. 5. For example, when an oscillation frequency of the laser pulse is 50 Hz, the capturing of one image by the camera 233 is also set at 50 Hz, and initiation of the image capturing is synchronized to the timing of the laser pulse oscillation. Thus, the fluorescent image for every one pulse is captured by the camera 233. The image captured by the camera 233 is, as shown in FIG. 6A, stored in the memory 209*c* as an image having luminance distribution for each laser pulse. In addition, by summing ten images from the first pulse to the tenth pulse, the luminance distribution in the ablation area limited by the opening of the circular aperture 218 is obtained as shown in FIG. 6B. That luminance distribution represents the irradiation intensity distribution of the laser beam at one scan.

Basically, the irradiation intensity distribution in the objective ablation area may be obtained by one scan; however, the irradiation apparatus 200 consistent with the present embodiment changes the moving (scanning) direction of the laser beam in a rectangular shape at every angle of 60 degrees (six scans cover one lap). Therefore, the irradiation intensity distribution within the ablation area for one scan may be obtained by irradiating the laser beam onto the fluorescent glass 10 for six scans with changing the moving (scanning) direction, and then summing and averaging the luminance distributions at each of the scans.

Besides, in the case of capturing the fluorescent image, it is preferable to previously provide a sensitivity correction to each pixel of the camera 233 In addition, it is preferable to previously capture an image before the laser irradiation is performed on the fluorescent glass 10, and provide a differential processing to it and the fluorescent image actually captured by the laser irradiation. This precludes the influence of disturbance light and facilitates obtaining only the luminance information of the fluorescence. Further, at the time of capturing the fluorescent image, unnecessary illumination such as illumination light for observation is shut off. Incidentally, a positional standard for the irradiation intensity distribution obtained is determined based on an image-pickup position of the camera 233.

When the irradiation intensity distribution of the laser beam in the ablation area is obtained, the computer 209 employs it as fundamental data for adjusting the laser irradiation. The irradiation apparatus 200 is provided with an energy monitor for the purpose of energy stabilization of the laser beam emitted from the laser source 210, and is controlled by the control unit 250 so that a total energy amount per one pulse becomes constant. The laser beam, however, is uneven in its energy density at an irradiation position due to energy loss produced inside the optical system before reaching the irradiation position, and varies also over time. Therefore, in the present embodiment, a relationship between the energy density and an ablation rate is previously stored, and the laser irradiation is adjusted based on it. As for the relationship between the energy density per one shot (one pulse) of the excimer laser beam and the ablation depth per one shot (referred to as the "ablation rate" in this description), it is confirmed that in a range of 100 to 400 $mJ/cm^2$, as the energy density increases, the ablation depth also increases almost linearly. Further, for the corneal surgery, the energy density of around 200 $mJ/cm^2$ is employed.

Figure 9:
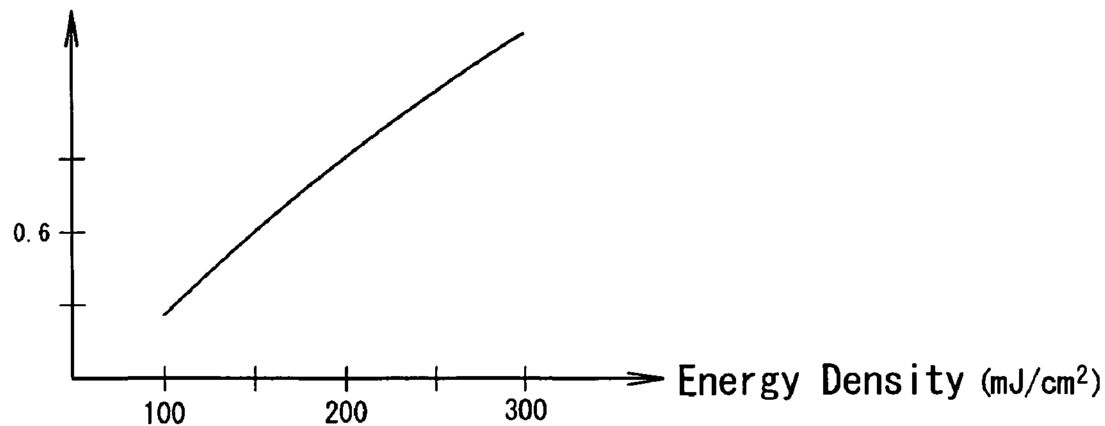
FIG. 9 is a view indicating a relationship between irradiation intensity of the laser beam and an ablation rate of a cornea.

The relationship of the ablation rate (ablation depth/one shot) with the irradiation intensity of the laser beam may be obtained as follows. For example, when a beam having the energy density of 150 $mJ/cm^2$ at its central part is irradiated onto the PMMA plate, if the ablation depth of 30 μ is obtained with 100 shots, the ablation rate in the case of the energy density being 150 $mJ/cm^2$ is 0.3 μ. Likewise, by obtaining the ablation rates for different values of the energy density, a table which shows the relationship of the ablation rate with the energy density is obtained. Further, it is empirically confirmed that the ablation rate of the cornea is approximately twice as that of the PMMA plate. Accordingly, if a table of the relationship between the irradiation intensity of the laser beam and the ablation rate of the cornea (see FIG. 9) is stored in memory means of the computer 209, the ablation rate corresponding to the irradiation intensity is obtained. Further, if a three-dimensional ablation shape of the cornea being an object to be processed is divided by the ablation rate determined based on the irradiation intensity distribution of the laser beam, distribution of the number of shots (the number of scans in the present apparatus) may be obtained. The laser irradiation may be adjusted by reflecting the unevenness of the irradiation intensity distribution as an increase or decrease in the number of shots.

Figure 7:
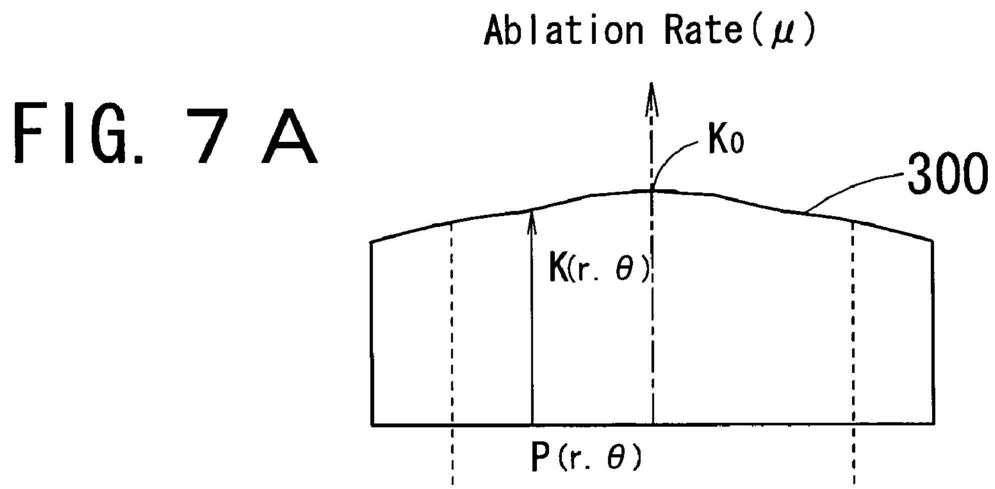
FIGS. 7A to 7C are views illustrating a method for calibrating data for ablation.
Figure 7:
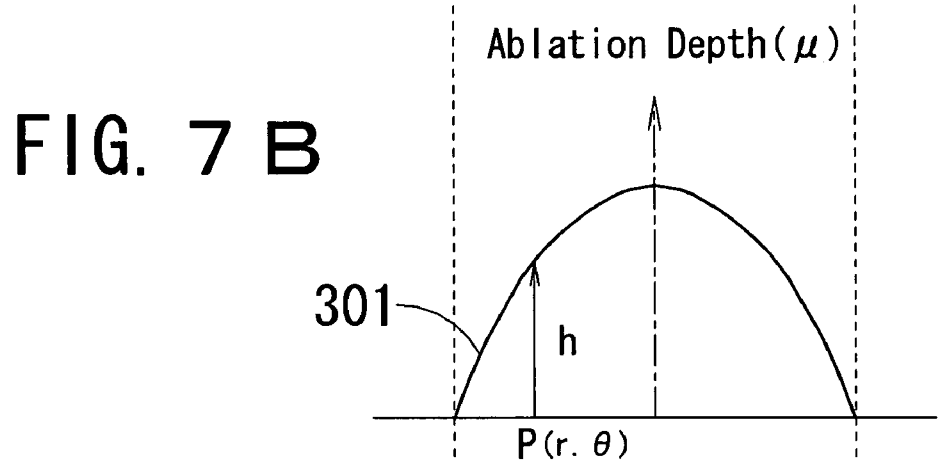
Figure 7:
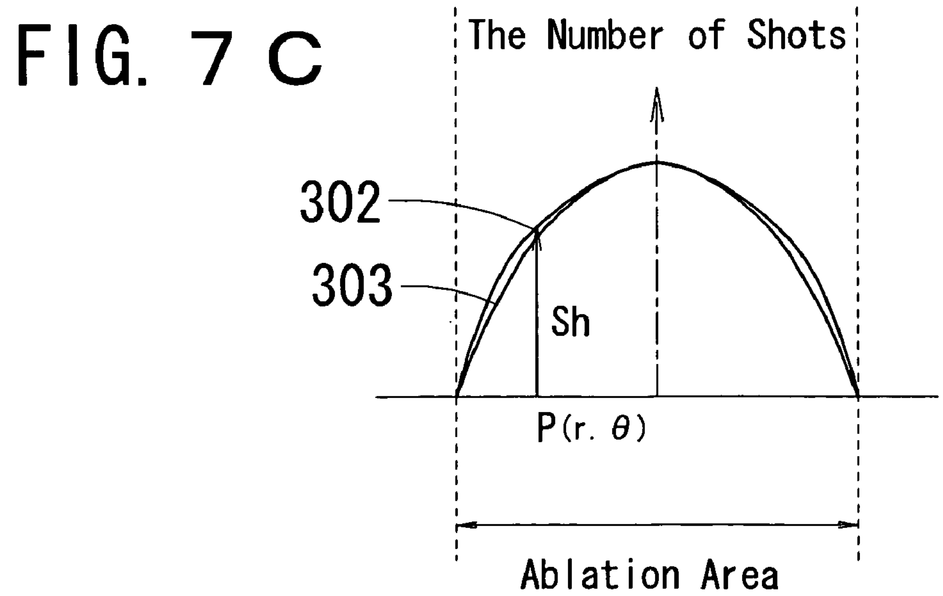

Here, the irradiation intensity distribution of the laser beam at an arbitrary angle θ corresponding to a certain meridian direction of the eye is assumed to be obtained as data 300 shown in FIG. 7A for a profile of the ablation rate. Then, the ablation rate at a position P (r, θ) which is at the angle θ, and a distance r from an irradiation center is assumed to be K(r, θ) . The value is utilized to calibrate the data for ablation. Assuming that the data for ablation at the angle θ is inputted as the ablation depth distribution data indicated as a graph 301 in FIG. 7B and the ablation depth at the position P (r, θ) is h, the number of shots $S_h$ after the correction is obtained by the following formula:

$$S_h = h/K(r, \theta).$$

When it is calculated for the whole ablation area, it is corrected to be distribution data on the number of shots indicated as a graph 302 in FIG. 7C. Incidentally, a graph 303 in FIG. 7C indicates distribution data on the number of shots where the ablation rate $K_0$ at the irradiation center is considered to be constant in the whole ablation area.

In addition, the calibration of the data for ablation may be represented in a form of the ablation depth as follows, instead of being represented as the distribution data on the number of shots. If the ablation rate at the center at which the ablation rate is a maximum value in FIG. 7A is taken as $K_0$, a changing ratio of the ablation rate at the position P (r, θ) with respect to $K_0$ is K (r, θ)/$K_0$. If the ablation depth at the position P (r, θ) is h as with FIG. 7B, the ablation depth h' after the correction is obtained by the following formula:

$$h' = h/(K(r,\theta)/K_0).$$

Figure 8:
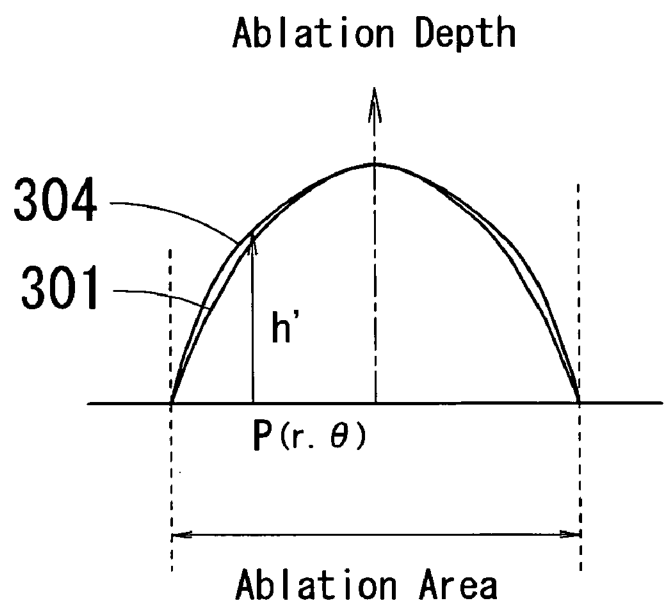
FIG. 8 is a view illustrating the method for calibrating data for ablation represented in the form of ablation depth.

When it is calculated for the whole ablation area, it is corrected to be the ablation depth distribution data indicated as a graph 304 in FIG. 8.

Besides, the data for ablation is obtained by obtaining the post-operative corneal shape where a lens component corresponding to an objective correction amount (a correction amount for correcting SPH, CYL, or Axis being subjective values or objective values, or a correction amount for correcting aberration of the eye) is removed from the pre-operative corneal shape previously measured, and by calculating a difference between the pre-operative and post-operative corneal shapes. The data for ablation is obtained by the computer 209 based on the pre-operative corneal shape inputted by the input unit 209*a* and the objective correction amount; however, the data calculated by another analyzer may be inputted to the computer 209.

Based on the distribution data on the number of shots after the correction (or the distribution data on the ablation depth after the correction), the computer 209 calibrates driving information for each of the driving units 214, 216, 219, 221, 268, and the like that change the position of the irradiation area and the ablation area. The distribution data on the number of shots (or the distribution data on the ablation depth) are divided into the rotationally symmetric component represented by the spherical component, the linearly symmetric component represented by the cylindrical component, and the asymmetric component other than those components. As for the rotationally symmetric component, the opening diameter of the circular aperture 218 per one scan is obtained. Similarly, as for the linearly symmetric component, the opening width of the slit aperture 220 per one scan is obtained. As for the asymmetric component, the travel position of the dividing aperture plate 260 and the closing and opening of the dividing shutter 265 per one scan are obtained. At the time of the actual ablation, each driving unit is controlled by the control unit 250 based on control data being a result of calculation by the computer 209.

Incidentally, as for the ablation of the rotationally symmetric component or the linear symmetric component, instead of controlling the circular aperture 218 or the slit aperture 220, the movement of the laser beam of which the cross section is in a rectangular shape, and the number of shots at each irradiation position may be controlled as described in U.S. Pat. No. 5,800,424 corresponding to Japanese Patent Unexamined Publications Nos. Hei8-66420 and Hei9-122167. Besides, needless to say, the number of shots may be treated as irradiation time of the laser beam. The number of shots or the irradiation time may be controlled by controlling the laser source 210.

The above-described laser irradiation apparatus has a constitution where the position of the irradiation area and the ablation area are changed by the translational scan of the laser beam and the control of the aperture 218 and the like. However, it may be an apparatus of such type that changes a spot position (position of the irradiation area) of the laser beam by an optical system which scans the laser beam formed into a small spot of about 0.1 to 1 mm (it may be constituted by two galvano-mirrors or the like) in the X and Y directions. Also in this type of apparatus, in the calibration mode, the laser beam is scanned so as to ablate with the constant depth distribution within the ablation area required for a corneal surgery, and the image on the camera 233 is captured in synchronization with the laser pulse oscillation signal. Then, the captured images are summed, so that the irradiation intensity distribution of the laser beam in one scan (one plane) of the ablation area is obtained. The laser irradiation may be adjusted by correcting the data for ablation or correcting the distribution data on the number of shots (irradiation time) at each irradiation position as previously described based on a change in the ablation rate distribution obtained by the irradiation intensity distribution. Further, in an apparatus of such type that irradiates a laser beam in a large spot, the laser irradiation may be adjusted by correcting the data for ablation or controlling the ablation area (irradiation area) as previously described.

As described above, according to the present invention, the irradiation intensity distribution of the laser beam is easily obtained and more accurate ablation may be performed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for ablating a cornea of a patient's eye by irradiation of an ultraviolet laser beam onto the cornea, the apparatus comprising:

irradiation means having a laser source for emitting the laser beam and an irradiation optical system for irradiating the laser beam emitted from the laser source onto the cornea;

an observation optical system having an objective lens, for observing the patient's eye;

input means for inputting corneal ablation data for ablating the cornea into a desired corrected shape;

calculation means for obtaining corneal ablation control data for the irradiation means based on the inputted corneal ablation data;

a fluorescent glass for calibration including a glass component and a rare-earth component, the fluorescent glass being disposed in an optical path of the irradiation optical system;

a fluorescence detecting optical system having an area sensor having a sensitivity to fluorescence, for obtaining an intensity distribution of the fluorescence emitted from the fluorescent glass by irradiation of the laser beam onto the fluorescent glass, the fluorescence detecting optical system detecting the fluorescence passed through the objective lens;

mode setting means for setting a calibration mode in which the irradiation means is controlled to ablate a predetermined ablation area at a constant ablation depth so as to calibrate variation of irradiation intensity distribution of the laser beam; and calibration means, when the calibration mode is set and the laser beam is irradiated by the irradiation means controlled to ablate the predetermined ablation area at the constant ablation depth, for calibrating at least one of the corneal ablation data and the corneal ablation control data based on the intensity distribution of the fluorescence obtained by the fluorescence detecting optical system.

2. The apparatus according to claim 1, further comprising a light source for anterior-segment illumination which is turned off when the calibration mode is set.

3. The apparatus according to claim 1, wherein the intensity distribution of the fluorescence is obtained by providing a differential processing to an image including the fluorescence and an image including no fluorescence.

* * * * *